US010590449B2

(12) United States Patent
Retsina et al.

(10) Patent No.: US 10,590,449 B2
(45) Date of Patent: Mar. 17, 2020

(54) HYDROTHERMAL-MECHANICAL TREATMENT OF LIGNOCELLULOSIC BIOMASS FOR PRODUCTION OF FERMENTATION PRODUCTS

(71) Applicant: API Intellectual Property Holdings, LLC, Atlanta, GA (US)

(72) Inventors: Theodora Retsina, Atlanta, GA (US); Jean-Pierre Bousquet, Peachtree Corners, GA (US)

(73) Assignees: GranBio Intellectual Property Holdings, Atlanta, GA (US); Valmet AB, Sundsvall (SE)

( * ) Notice: Subject to any disclaimer, the term of this patent is extended or adjusted under 35 U.S.C. 154(b) by 0 days.

(21) Appl. No.: 15/177,385

(22) Filed: Jun. 9, 2016

(65) Prior Publication Data

US 2016/0362713 A1 Dec. 15, 2016

Related U.S. Application Data

(60) Provisional application No. 62/173,217, filed on Jun. 9, 2015.

(51) Int. Cl.

| | |
|---|---|
| *C12P 19/14* | (2006.01) |
| *C12P 19/02* | (2006.01) |
| *C12P 7/10* | (2006.01) |
| *C12P 7/14* | (2006.01) |
| *C12P 7/16* | (2006.01) |
| *C12P 7/18* | (2006.01) |
| *C12P 7/46* | (2006.01) |
| *C12P 7/56* | (2006.01) |

(52) U.S. Cl.
CPC ............ *C12P 19/14* (2013.01); *C12P 7/10* (2013.01); *C12P 7/14* (2013.01); *C12P 7/16* (2013.01); *C12P 7/18* (2013.01); *C12P 7/46* (2013.01); *C12P 7/56* (2013.01); *C12P 19/02* (2013.01); *C12P 2203/00* (2013.01); *Y02E 50/10* (2013.01); *Y02E 50/16* (2013.01); *Y02E 50/17* (2013.01)

(58) Field of Classification Search
CPC .... C12P 19/14; C12P 7/10; C12P 7/14; C12P 7/16; C12P 7/18; C12P 7/46; C12P 7/56; C12P 19/02; C12P 2203/00; Y02E 50/10; Y02E 50/16; Y02E 50/17

USPC .......................................................... 435/99
See application file for complete search history.

(56) References Cited

U.S. PATENT DOCUMENTS

| | | | |
|---|---|---|---|
| 2010/0313882 A1 | 12/2010 | Dottori et al. | |
| 2012/0006320 A1* | 1/2012 | Nguyen | D21C 1/00 127/34 |
| 2013/0244291 A1* | 9/2013 | Retsina | C13K 13/007 435/99 |
| 2015/0079639 A1 | 3/2015 | Retsina et al. | |

FOREIGN PATENT DOCUMENTS

WO 2015017869 A1 2/2015

OTHER PUBLICATIONS

International Preliminary Report on Patentability, Chapter I of PCT, PCT/US2016/036571, The International Bureau of WIPO, dated Dec. 12, 2017.
Chaturvedi et al., "An overview of key pretreatment processes employed for bioconversion of lignocellulosic biomass into biofuels and value added product", 3 Biotech, 2013, 3:415-431.

* cited by examiner

*Primary Examiner* — Jennifer M.H. Tichy
(74) *Attorney, Agent, or Firm* — O'Connor & Company; Ryan P. O'Connor

(57) ABSTRACT

A simple process for converting lignocellulosic biomass into fermentation products is disclosed. Biomass may be subjected to a steam or hot-water soak to dissolve hemicelluloses. This step is followed by mechanical refining, such as in a hot-blow refiner, of the cellulose-rich (and lignin-rich) solids. The refined solids are then enzymatically hydrolyzed to generate sugars. Certain embodiments provide a process for producing ethanol, comprising: digesting a cellulosic biomass feedstock with steam or hot water to produce cellulose-rich solids, hemicellulose oligomers, and lignin; conveying the digested stream through a blow-line refiner; separating a vapor from the refined stream; introducing the refined stream to an enzymatic hydrolysis unit to produce sugars; fermenting the sugars to produce ethanol in dilute solution; and concentrating the dilute solution to produce an ethanol product. Enzymes and microorganisms may be introduced at various points in the process. The invention may be applied to any other fermentation product.

17 Claims, 3 Drawing Sheets

HYDROTHERMAL-MECHANICAL TREATMENT OF LIGNOCELLULOSIC BIOMASS FOR PRODUCTION OF FERMENTATION PRODUCTS

PRIORITY DATA

This patent application is a non-provisional application claiming priority to U.S. Provisional Patent App. No. 62/173,217, filed on Jun. 9, 2015, which is hereby incorporated by reference herein.

FIELD OF THE INVENTION

The present invention generally relates to processes for preparing fermentable sugars from lignocellulosic biomass.

BACKGROUND OF THE INVENTION

The Green Power+® technology has been developed by American Process, Inc. This technology extracts hemicelluloses from a biomass feedstock supply and converts only those hemicelluloses into sugars which are then fermented, such as to cellulosic ethanol. Green Power+ technology is a two-step process to produce sugars from hemicelluloses. An initial steam or hot-water extraction pulls out hemicelluloses, and the remainder of the biomass (cellulose/lignin) is not exposed to any acidic treatment. The remaining solids remain suitable for combustion in a boiler or for pelletization, or other uses. The extracted solution is then hydrolyzed with a mild acid or enzyme treatment to hydrolyze oligomers into fermentable monomers.

The biomass that has been extracted of hemicelluloses is suitable for a variety of downstream applications, including combustion in biomass boilers, combined heat and power, torrefaction, pelleting, pulping, or production of specialty products (e.g. panels). Co-location with a biomass power plant leads to synergies and cost advantages.

What are desired are variations of the Green Power+ technology that obtain sugars from the cellulose portion of the starting biomass feedstock. Low-cost methods are desired to produce biomass sugars for conversion to ethanol, n-butanol, and other fuels and chemicals.

SUMMARY OF THE INVENTION

The present invention addresses the aforementioned needs in the art.

In some variations, a process is provided for producing fermentable sugars from cellulosic biomass, the process comprising:
  (a) providing a feedstock comprising cellulosic biomass;
  (b) digesting the feedstock with a reaction solution including steam and/or hot water in a digestor under effective reaction conditions to produce a digested stream containing cellulose-rich solids, hemicellulose oligomers, and lignin;
  (c) conveying the digested stream through a mechanical refiner, thereby generating a refined stream with reduced average particle size of the cellulose-rich solids;
  (d) separating a vapor from the refined stream;
  (e) introducing the refined stream to an enzymatic hydrolysis unit under effective hydrolysis conditions to produce sugars from the cellulose-rich solids and optionally from the hemicellulose oligomers; and
  (f) recovering or further processing at least some of the sugars as fermentable sugars.

In some embodiments, the reaction solution comprises steam in saturated, superheated, or supersaturated form. In these or other embodiments, the reaction solution comprises hot water.

The mechanical refiner may be selected from the group consisting of a hot-blow refiner, a hot-stock refiner, a blow-line refiner, a disk refiner, a conical refiner, a cylindrical refiner, an in-line defibrator, a homogenizer, and combinations thereof (noting that these industry terms are not mutually exclusive to each other). In certain embodiments, the mechanical refiner is a blow-line refiner.

In some embodiments, a blow tank is situated downstream of the mechanical refiner. In other embodiments, a blow tank is situated upstream of the mechanical refiner. The vapor separated in step (d) may be separated from the blow tank.

In some embodiments, heat is recovered from at least some of the vapor. At least some of the vapor may be compressed and returned to the digestor. Some of the vapor may be purged from the process.

In some embodiments, enzymes introduced or present in the enzymatic hydrolysis unit may include not only cellulases but also hemicellulases. In certain embodiments, enzymes introduced or present in the enzymatic hydrolysis unit include endoglucanases and exoglucanases.

The reaction solution optionally includes an acid catalyst, to assist in extraction of hemicelluloses from the starting material, and possibly to catalyze some hydrolysis. In some embodiments, the acid is a sulfur-containing acid (e.g., sulfur dioxide). In some embodiments, the acid is acetic acid, which may be recovered from the digested stream (i.e., from downstream operations).

The starting feedstock may include sucrose, such as in the case of energy cane. A majority of the sucrose may be recovered or fermented as part of the fermentable sugars.

The process may further include removal of one or more fermentation inhibitors by stripping. This stripping may be conducted following step (e), i.e. treating the hydrolyzed cellulose stream, prior to fermentation. Alternatively, or additionally, the stripping may be conducted on a stream following digestion, such as in the blow line, or as part of an acetic acid recycle system.

The process may further include a step of fermenting the fermentable sugars to a fermentation product. Typically the process will further include concentration and purification of the fermentation product. The fermentation product may be selected from ethanol, n-butanol, 1,4-butanediol, succinic acid, lactic acid, or combinations thereof, for example. The lignin may be combusted for energy production.

Some variations provide a process for producing fermentable sugars from cellulosic biomass, the process comprising:
  (a) providing a feedstock comprising cellulosic biomass;
  (b) digesting the feedstock with a reaction solution including steam and/or hot water in a digestor under effective reaction conditions to produce a digested stream containing cellulose-rich solids, hemicellulose oligomers, and lignin;
  (c) conveying the digested stream through a mechanical refiner, thereby generating a refined stream with reduced average particle size of the cellulose-rich solids;
  (d) separating a vapor from the refined stream;
  (e) introducing the refined stream to an acid hydrolysis unit under effective hydrolysis conditions to produce sugars from the cellulose-rich solids and optionally from the hemicellulose oligomers;

(f) recovering or further processing at least some of the sugars as fermentable sugars.

Certain embodiments provide a process for producing ethanol from cellulosic biomass, the process comprising:

(a) providing a feedstock comprising cellulosic biomass;
(b) digesting the feedstock with a reaction solution including steam and/or hot water in a digestor under effective reaction conditions to produce a digested stream containing cellulose-rich solids, hemicellulose oligomers, and lignin;
(c) conveying the digested stream through a blow-line refiner, thereby generating a refined stream with reduced average particle size of the cellulose-rich solids;
(d) separating a vapor from the refined stream;
(e) introducing the refined stream to an enzymatic hydrolysis unit under effective hydrolysis conditions to produce sugars from the cellulose-rich solids and from the hemicellulose oligomers;
(f) fermenting the sugars to produce ethanol in dilute solution; and
(g) concentrating the dilute solution to produce an ethanol product.

Some variations provide a process for producing a fermentation product from biomass, the process comprising:

(a) providing a feedstock containing lignocellulosic biomass and monomeric sugar that is physically bound therein;
(b) combining the feedstock with a sugar-fermenting microorganism and optionally cellulase enzymes, to create an initial mixture;
(c) refining the initial mixture to mechanically release the monomeric sugar and to intimately mix the sugar-fermenting microorganism and, if present, the cellulase enzymes;
(d) fermenting the monomeric sugar with the sugar-fermenting microorganism to produce an initial quantity of a fermentation product contained within an intermediate mixture;
(e) digesting the intermediate mixture with a reaction solution including steam and/or hot water in a digestor under effective reaction conditions to produce a digested stream containing cellulose-rich solids, hemicellulose oligomers, and lignin;
(f) optionally conveying the digested stream through a mechanical refiner to reduce average particle size of the cellulose-rich solids;
(g) separating a vapor from the digested stream and recovering the fermentation product from the vapor;
(h) introducing the digested stream to an enzymatic hydrolysis unit under effective hydrolysis conditions to produce cellulosic sugars from the cellulose-rich solids and optionally from the hemicellulose oligomers; and
(i) fermenting the cellulosic sugars to produce an additional quantity of the fermentation product.

In some embodiments, the feedstock includes sugarcane, energy cane, or combinations thereof, and the monomeric sugar is substantially sucrose. In these or other embodiments, the feedstock includes corn, and the monomeric sugar is substantially dextrose.

The sugar-fermenting microorganism may be a yeast or bacteria.

The reaction solution may include steam in saturated, superheated, or supersaturated form. In some embodiments, the reaction solution comprises hot water. The reaction solution may further comprise an acid, such as a sulfur-containing acid or acetic acid (e.g., acetic acid recovered from the digested stream).

The mechanical refiner may be selected from the group consisting of a hot-blow refiner, a hot-stock refiner, a blow-line refiner, a disk refiner, a conical refiner, a cylindrical refiner, an in-line defibrator, a homogenizer, and combinations thereof. In some embodiments with step (f), a blow tank is situated downstream of the mechanical refiner and/or a blow tank is situated upstream of the mechanical refiner.

In some embodiments, vapor is separated from a blow tank, and heat is recovered from at least some of the vapor. At least some of the vapor may be compressed and returned to the digestor. Some vapor may be purged from the process.

Enzymes introduced or present in the enzymatic hydrolysis unit may include cellulases and hemicellulases. Enzymes introduced or present in the enzymatic hydrolysis unit may include endoglucanases and exoglucanases.

The fermentation product may be selected from ethanol, n-butanol, 1,4-butanediol, succinic acid, lactic acid, or combinations thereof. In some embodiments, the fermentation product is ethanol. The process may include concentration and purification of the fermentation product. The process may further include combusting the lignin.

Some variations provide a process for producing a fermentation product from biomass, the process comprising:

(a) providing a feedstock containing lignocellulosic biomass and monomeric sugar that is physically bound therein;
(b) combining the feedstock with a sugar-fermenting microorganism and cellulase enzymes, to create an initial mixture;
(c) refining the initial mixture to mechanically release the monomeric sugar and to intimately mix the sugar-fermenting microorganism and the cellulase enzymes;
(d) fermenting the monomeric sugar with the sugar-fermenting microorganism to produce an initial quantity of a fermentation product contained within an intermediate mixture;
(e) digesting the intermediate mixture with a reaction solution including steam and/or hot water in a digestor under effective reaction conditions to produce a digested stream containing cellulose-rich solids, hemicellulose oligomers, and lignin;
(f) conveying the digested stream through a mechanical refiner to reduce average particle size of the cellulose-rich solids;
(g) introducing the digested stream to an enzymatic hydrolysis unit under effective hydrolysis conditions to produce cellulosic sugars from the cellulose-rich solids and optionally from the hemicellulose oligomers; and
(h) fermenting the cellulosic sugars to produce an additional quantity of the fermentation product.

Some variations provide a process for producing a fermentation product from biomass, the process comprising:

(a) providing a feedstock containing lignocellulosic biomass and monomeric sugar that is physically bound therein;
(b) combining the feedstock with a sugar-fermenting microorganism, to create an initial mixture;
(c) refining the initial mixture to mechanically release the monomeric sugar and to intimately mix the sugar-fermenting microorganism;
(d) fermenting the monomeric sugar with the sugar-fermenting microorganism to produce an initial quantity of a fermentation product contained within an intermediate mixture;

(e) digesting the intermediate mixture with a reaction solution including steam and/or hot water in a digestor under effective reaction conditions to produce a digested stream containing cellulose-rich solids, hemicellulose oligomers, and lignin;

(f) introducing the digested stream to an enzymatic hydrolysis unit under effective hydrolysis conditions to produce cellulosic sugars from the cellulose-rich solids and optionally from the hemicellulose oligomers; and (g) fermenting the cellulosic sugars to produce an additional quantity of the fermentation product.

Some variations provide a process for producing ethanol from biomass, the process comprising:

(a) providing a feedstock containing sugarcane or energy cane with sucrose physically bound therein;

(b) combining the feedstock with a sugar-fermenting microorganism and optionally cellulase enzymes, to create an initial mixture;

(c) refining the initial mixture to mechanically release the sucrose and to intimately mix the sugar-fermenting microorganism and, if present, the cellulase enzymes;

(d) fermenting the sucrose with the sugar-fermenting microorganism to produce an initial quantity of ethanol contained within an intermediate mixture;

(e) digesting the intermediate mixture with a reaction solution including steam and/or hot water in a digestor under effective reaction conditions to produce a digested stream containing cellulose-rich solids, hemicellulose oligomers, and lignin;

(f) optionally conveying the digested stream through a mechanical refiner to reduce average particle size of the cellulose-rich solids;

(g) separating a vapor from the digested stream and recovering at least some of the initial quantity of ethanol from the vapor;

(h) introducing the digested stream to an enzymatic hydrolysis unit under effective hydrolysis conditions to produce cellulosic sugars from the cellulose-rich solids and optionally from the hemicellulose oligomers; and (i) fermenting the cellulosic sugars to produce an additional quantity of ethanol.

DETAILED DESCRIPTION OF EMBODIMENTS OF THE INVENTION

Figure 1:
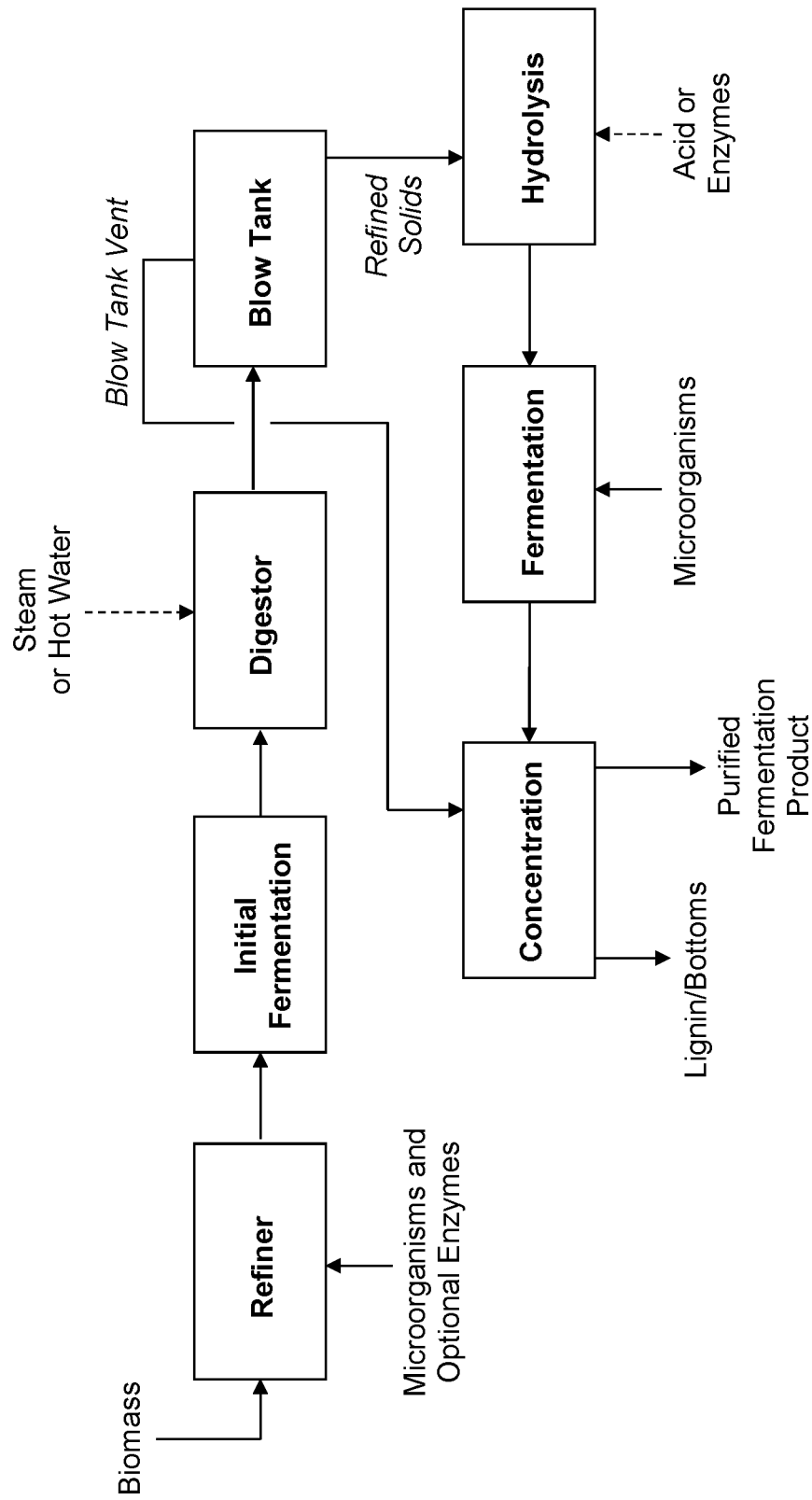
FIG. 1 is a simplified block-flow diagram depicting the process of some embodiments of the present invention.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

All descriptions of embodiments of the invention shall be construed as embodiments that are "characterized by" the applicable description(s) or "characterized in that" the embodiments include the applicable description(s).

Some variations are premised on the discovery of a surprisingly simple process for converting lignocellulosic biomass into fermentable sugars. Biomass may be subjected to a steam or hot-water soak to dissolved hemicelluloses, with or without acetic acid recycle. This step is followed by mechanical refining, such as in a hot-blow refiner, of the cellulose-rich (and lignin-rich) solids. The refined solids are then enzymatically hydrolyzed to generate sugars. A stripping step for removing fermentation inhibitors in the hydrolysate may be included.

Certain exemplary embodiments of the invention will now be described. These embodiments are not intended to limit the scope of the invention as claimed. The order of steps may be varied, some steps may be omitted, and/or other steps may be added. Reference herein to first step, second step, etc. is for illustration purposes only. In the drawings, dotted lines denote optional streams.

In some variations, a process is provided for producing fermentable sugars from cellulosic biomass, the process comprising:

(a) providing a feedstock comprising cellulosic biomass;

(b) digesting the feedstock with a reaction solution including steam and/or hot water in a digestor under effective reaction conditions to produce a digested stream containing cellulose-rich solids, hemicellulose oligomers, and lignin;

(c) conveying the digested stream through a mechanical refiner, thereby generating a refined stream with reduced average particle size of the cellulose-rich solids;

(d) separating a vapor from the refined stream;

(e) introducing the refined stream to an enzymatic hydrolysis unit under effective hydrolysis conditions to produce sugars from the cellulose-rich solids and optionally from the hemicellulose oligomers; and (f) recovering or further processing at least some of the sugars as fermentable sugars.

In some embodiments, the reaction solution comprises steam in saturated, superheated, or supersaturated form. In these or other embodiments, the reaction solution comprises hot water.

The mechanical refiner may be selected from the group consisting of a hot-blow refiner, a hot-stock refiner, a blow-line refiner, a disk refiner, a conical refiner, a cylindrical refiner, an in-line defibrator, a homogenizer, and combinations thereof (noting that these industry terms are not mutually exclusive to each other). In certain embodiments, the mechanical refiner is a blow-line refiner. Other mechanical refiners may be employed, and chemical refining aids may be introduced.

Mechanically treating (refining) may employ one or more known techniques such as, but by no means limited to, milling, grinding, beating, sonicating, or any other means to reduce cellulose particle size. Such refiners are well-known in the industry and include, without limitation, Valley beaters, single disk refiners, double disk refiners, conical refiners, including both wide angle and narrow angle, cylindrical refiners, homogenizers, microfluidizers, and other similar milling or grinding apparatus. See, for example, Smook, *Handbook for Pulp & Paper Technologists*, Tappi Press, 1992.

In some embodiments, a blow tank is situated downstream of the mechanical refiner. In other embodiments, a blow tank is situated upstream of the mechanical refiner. In certain embodiments, a first blow tank is situated downstream of the mechanical refiner and a second blow tank is situated upstream of the mechanical refiner. The vapor separated in step (d) may be separated from a blow tank.

Note that "blow tank" should be broadly construed to include not only a tank but any other apparatus or equipment capable of allowing a pressure reduction in the process stream. Thus a blow tank may be a tank, vessel, section of pipe, valve, separation device, or other unit.

In some embodiments, following a digestor to remove hemicellulose, an intermediate blow is performed to, for example, about 40 psig. The material is sent to a blowline refiner, and then to a final blow to atmospheric pressure.

The refining may be conducted at a wide range of solids concentrations (consistency), including from about 5% to about 50% consistency, such as about 10%, 20%, 30%, 35%, or 40% consistency.

In some embodiments, heat is recovered from at least some of the vapor, using the principles of heat integration. At least some of the vapor may be compressed and returned to the digestor. Some of the vapor may be purged from the process.

The reaction solution optionally includes an acid catalyst, to assist in extraction of hemicelluloses from the starting material, and possibly to catalyze some hydrolysis. In some embodiments, the acid is a sulfur-containing acid (e.g., sulfur dioxide). In some embodiments, the acid is acetic acid, which may be recovered from the digested stream (i.e., from downstream operations).

The starting feedstock may include sucrose, such as in the case of energy cane. A majority of the sucrose may be recovered as part of the fermentable sugars.

The process may include cleaning the starting feedstock, by wet or dry cleaning. The process may include size reduction, hot-water soaking, dewatering, steaming, or other operations, upstream of the digestor.

In some embodiments, enzymes introduced or present in the enzymatic hydrolysis unit may include not only cellulases but also hemicellulases. In certain embodiments, enzymes introduced or present in the enzymatic hydrolysis unit include endoglucanases and exoglucanases.

The process may further include removal of one or more fermentation inhibitors (such as acetic acid or furfural) by stripping. This stripping may be conducted following step (e), i.e. treating the hydrolyzed cellulose stream, prior to fermentation. Alternatively, or additionally, the stripping may be conducted on a stream following digestion, such as in the blow line, or as part of an acetic acid recycle system.

The process may further include a step of fermenting the fermentable sugars to a fermentation product. Typically the process will further include concentration and purification of the fermentation product. The fermentation product may be selected from ethanol, n-butanol, 1,4-butanediol, succinic acid, lactic acid, or combinations thereof, for example. The lignin may be combusted for energy production.

Some variations are premised on the realization that enzymes and/or microorganisms (e.g., yeast, yeast spores, bacteria, etc.) may be added at various points in the process. Early addition of microorganisms may be particularly advantageous when free sugar is present or readily released in the starting feedstock. For example, sugarcane or energy cane contain free sugar in the form of sucrose (in extractable juice), and this sucrose can be fermented to ethanol or another product prior to enzymatic hydrolysis of the cellulose to glucose and/or during enzymatic hydrolysis of the cellulose to glucose. Some embodiments introduce cellulase enzymes along with microorganisms to a mixture which is then refined or mechanically treated, or to a mixture which is undergoing refining or other mechanical treatment.

In some embodiments, such as depicted in FIG. 1, a microorganism such as yeast is added along with feedstock (e.g., sugarcane or energy cane) to a refiner or other mechanical device. The refiner is configured to mix vigorously to enable intimate contact and crushing of the feedstock. The refiner also gives intimate contact of the microorganism with juice and dry matter. The refiner may be operated at atmospheric conditions. This disclosure incorporates by reference commonly owned U.S. patent application Ser. No. 14/487,070 for Retsina et al., "PROCESSES AND APPARATUS FOR REFINING SUGARCANE TO PRODUCE SUGARS, BIOFUELS, AND/OR BIOCHEMICALS," filed Sep. 15, 2014, which discloses refiners that are suitable for some embodiments of the processes described herein.

Enzymes may be introduced to the refiner or to the feed stream into the refiner. An initial fermentation is then carried out to ferment the free sugar to ethanol or another fermentation product, which may be sent to purification or may remain in the mixture. In the embodiments shown in FIG. 1, the entire mixture (including ethanol or other product) proceeds to a steam or hot-water digestor for hemicellulose extraction. Then the digested material is conveyed to a blow tank, with or without intermediate blow-line refining, and the vent of the blow tank may be sent directly to rectification, distillation, or other purification unit. When the initial fermentation is ethanol, the blow tank vent will be enriched in ethanol, allowing for convenient recovery.

The initial fermentation may be achieved in an ordinary fermentor or another type of vessel, container, or pipe allowing for suitable retention time. The temperature will typically be about 25° C. to about 80° C., such as about 30° C. to about 50° C. Following the initial fermentation, the mixture may then be further treated at a higher temperature (and pressure) and/or a longer time. The material is then blown into a blow tank, optionally with refining before, during, or after such discharge.

Figure 2:
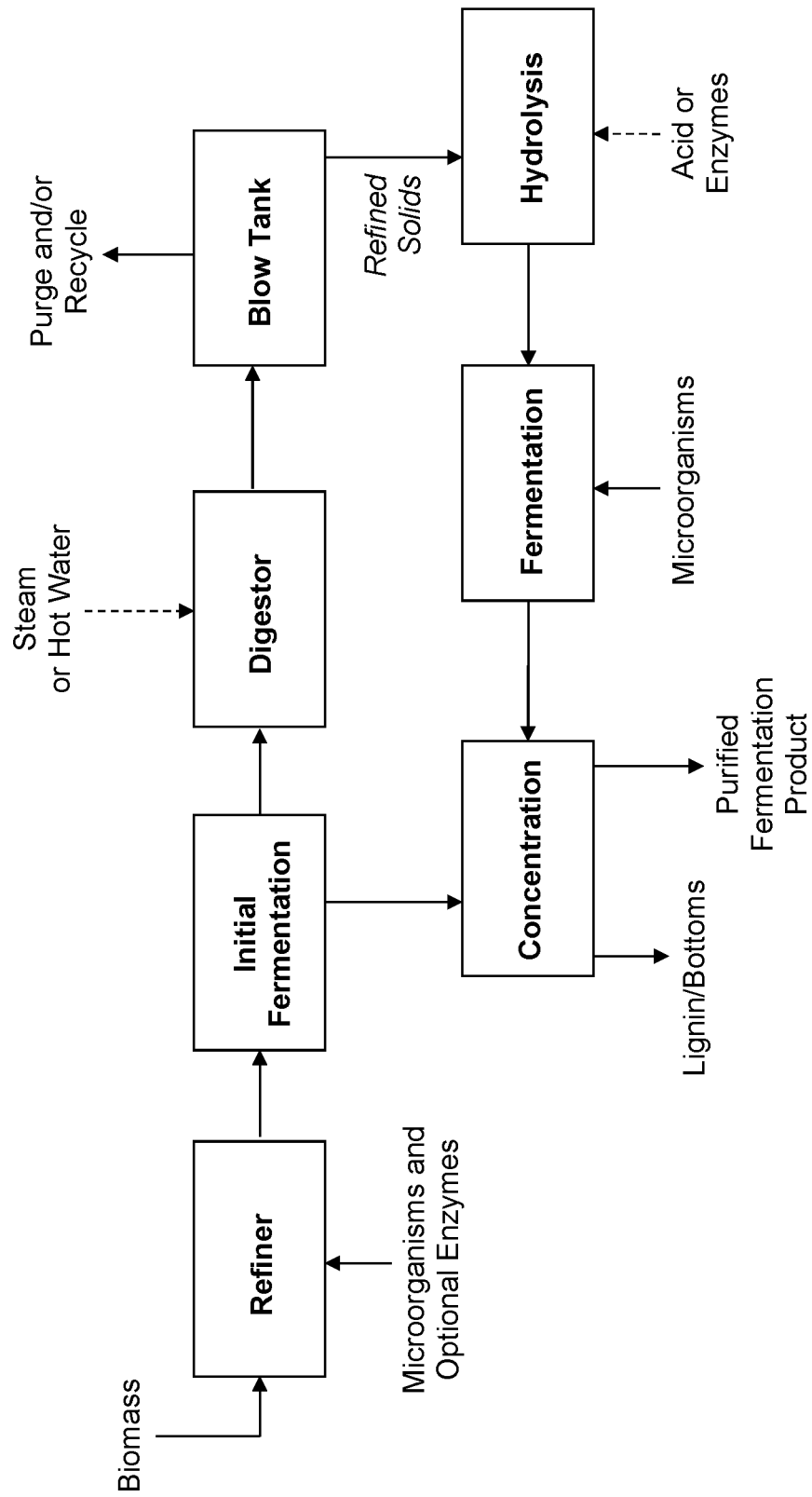
FIG. 2 is a simplified block-flow diagram depicting the process of some embodiments of the present invention.

In FIG. 2, the initial fermentation product is removed and sent directly to purification. When the initial fermentation product (from free sugar such as sucrose) is the same as the later fermentation product (from cellulosic sugars), a common purification system is preferably employed, but that is not necessary. In certain embodiments, a portion of the initial fermentation product is sent directly to purification while a portion is conveyed to the digestor and then recovered from the blow tank vent, in a combination of FIGS. 1 and 2.

Figure 3:
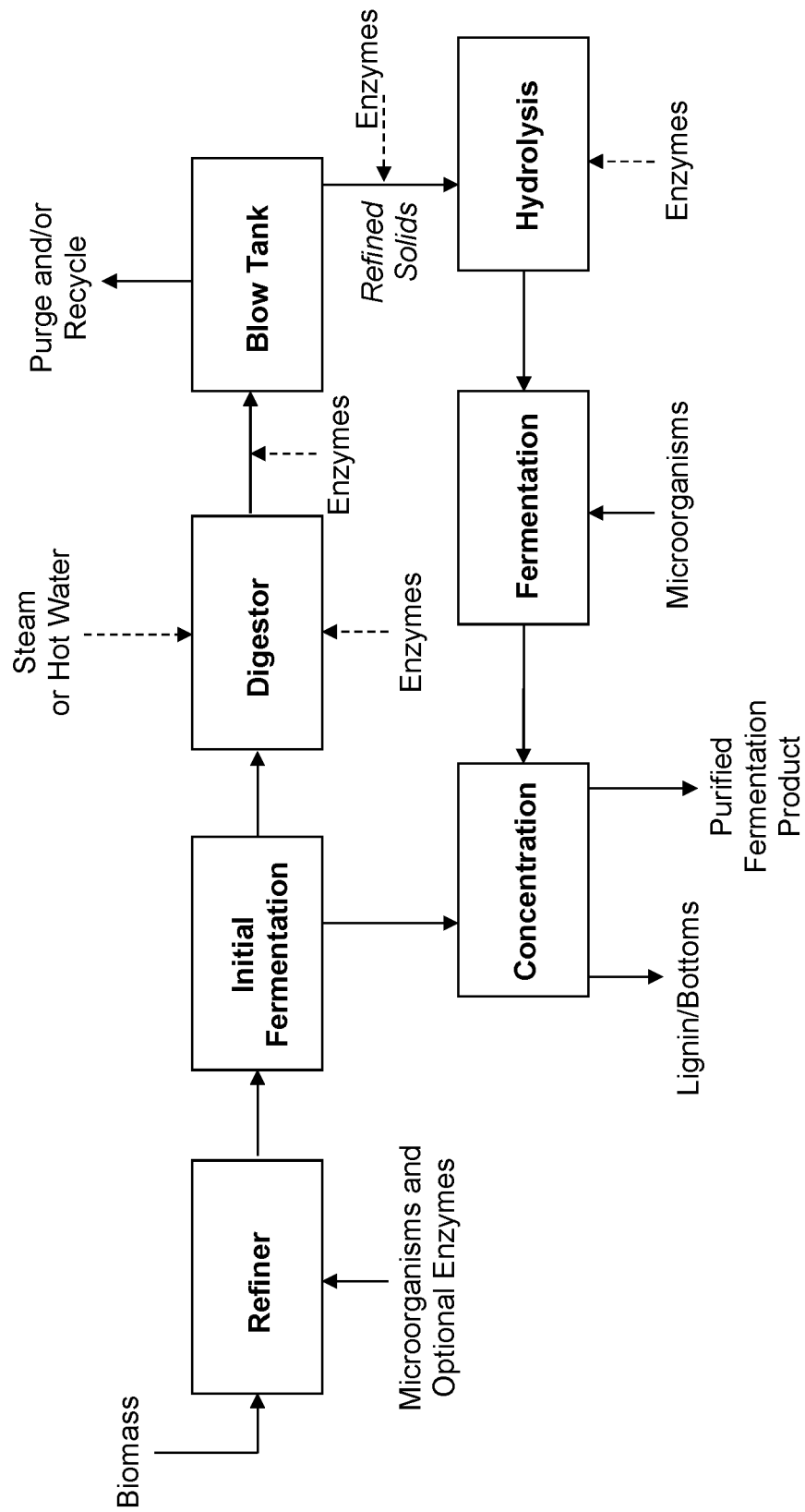
FIG. 3 is a simplified block-flow diagram depicting the process of some embodiments of the present invention.

FIG. 3 illustrates that enzymes may be introduced at many locations throughout the process. Enzymes may also be added to the blow line before the blow-line refiner (not shown) or at the blow-line refiner, to assist in enzyme contact with fibers. Microorganisms (such as yeasts or bacteria) may also be added at various locations.

Some variations provide a process for producing a fermentation product from biomass, the process comprising:
(a) providing a feedstock containing lignocellulosic biomass and monomeric sugar that is physically bound therein;
(b) combining the feedstock with a sugar-fermenting microorganism and optionally cellulase enzymes, to create an initial mixture;
(c) refining the initial mixture to mechanically release the monomeric sugar and to intimately mix the sugar-fermenting microorganism and, if present, the cellulase enzymes;
(d) fermenting the monomeric sugar with the sugar-fermenting microorganism to produce an initial quantity of a fermentation product contained within an intermediate mixture;
(e) digesting the intermediate mixture with a reaction solution including steam and/or hot water in a digestor under effective reaction conditions to produce a digested stream containing cellulose-rich solids, hemicellulose oligomers, and lignin;
(f) optionally conveying the digested stream through a mechanical refiner to reduce average particle size of the cellulose-rich solids;
(g) separating a vapor from the digested stream and recovering the fermentation product from the vapor;
(h) introducing the digested stream to an enzymatic hydrolysis unit under effective hydrolysis conditions to produce cellulosic sugars from the cellulose-rich solids and optionally from the hemicellulose oligomers; and
(i) fermenting the cellulosic sugars to produce an additional quantity of the fermentation product.

In some embodiments, the feedstock includes sugarcane, energy cane, or combinations thereof, and the monomeric sugar is substantially sucrose. In these or other embodiments, the feedstock includes corn, and the monomeric sugar is substantially dextrose.

The sugar-fermenting microorganism may be a yeast or bacteria.

The reaction solution may include steam in saturated, superheated, or supersaturated form. In some embodiments, the reaction solution comprises hot water. The reaction solution may further comprise an acid, such as a sulfur-containing acid or acetic acid (e.g., acetic acid recovered from the digested stream).

The mechanical refiner may be selected from the group consisting of a hot-blow refiner, a hot-stock refiner, a blow-line refiner, a disk refiner, a conical refiner, a cylindrical refiner, an in-line defibrator, a homogenizer, and combinations thereof. In some embodiments with step (f), a blow tank is situated downstream of the mechanical refiner and/or a blow tank is situated upstream of the mechanical refiner.

In some embodiments, vapor is separated from a blow tank, and heat is recovered from at least some of the vapor. At least some of the vapor may be compressed and returned to the digestor. Some vapor may be purged from the process.

Enzymes introduced or present in the enzymatic hydrolysis unit may include cellulases and hemicellulases. Enzymes introduced or present in the enzymatic hydrolysis unit may include endoglucanases and exoglucanases.

The fermentation product may be selected from ethanol, n-butanol, 1,4-butanediol, succinic acid, lactic acid, or combinations thereof. In some embodiments, the fermentation product is ethanol. The process may include concentration and purification of the fermentation product. The process may further include combusting the lignin.

Some variations provide a process for producing a fermentation product from biomass, the process comprising:
(a) providing a feedstock containing lignocellulosic biomass and monomeric sugar that is physically bound therein;
(b) combining the feedstock with a sugar-fermenting microorganism and cellulase enzymes, to create an initial mixture;
(c) refining the initial mixture to mechanically release the monomeric sugar and to intimately mix the sugar-fermenting microorganism and the cellulase enzymes;
(d) fermenting the monomeric sugar with the sugar-fermenting microorganism to produce an initial quantity of a fermentation product contained within an intermediate mixture;
(e) digesting the intermediate mixture with a reaction solution including steam and/or hot water in a digestor under effective reaction conditions to produce a digested stream containing cellulose-rich solids, hemicellulose oligomers, and lignin;
(f) conveying the digested stream through a mechanical refiner to reduce average particle size of the cellulose-rich solids;
(g) introducing the digested stream to an enzymatic hydrolysis unit under effective hydrolysis conditions to produce cellulosic sugars from the cellulose-rich solids and optionally from the hemicellulose oligomers; and
(h) fermenting the cellulosic sugars to produce an additional quantity of the fermentation product.

Some variations provide a process for producing a fermentation product from biomass, the process comprising:
(a) providing a feedstock containing lignocellulosic biomass and monomeric sugar that is physically bound therein;
(b) combining the feedstock with a sugar-fermenting microorganism, to create an initial mixture;

(c) refining the initial mixture to mechanically release the monomeric sugar and to intimately mix the sugar-fermenting microorganism;

(d) fermenting the monomeric sugar with the sugar-fermenting microorganism to produce an initial quantity of a fermentation product contained within an intermediate mixture;

(e) digesting the intermediate mixture with a reaction solution including steam and/or hot water in a digestor under effective reaction conditions to produce a digested stream containing cellulose-rich solids, hemicellulose oligomers, and lignin;

(f) introducing the digested stream to an enzymatic hydrolysis unit under effective hydrolysis conditions to produce cellulosic sugars from the cellulose-rich solids and optionally from the hemicellulose oligomers; and (g) fermenting the cellulosic sugars to produce an additional quantity of the fermentation product.

Some variations provide a process for producing ethanol from biomass, the process comprising:

(a) providing a feedstock containing sugarcane or energy cane with sucrose physically bound therein;

(b) combining the feedstock with a sugar-fermenting microorganism and optionally cellulase enzymes, to create an initial mixture;

(c) refining the initial mixture to mechanically release the sucrose and to intimately mix the sugar-fermenting microorganism and, if present, the cellulase enzymes;

(d) fermenting the sucrose with the sugar-fermenting microorganism to produce an initial quantity of ethanol contained within an intermediate mixture;

(e) digesting the intermediate mixture with a reaction solution including steam and/or hot water in a digestor under effective reaction conditions to produce a digested stream containing cellulose-rich solids, hemicellulose oligomers, and lignin;

(f) optionally conveying the digested stream through a mechanical refiner to reduce average particle size of the cellulose-rich solids;

(g) separating a vapor from the digested stream and recovering at least some of the initial quantity of ethanol from the vapor;

(h) introducing the digested stream to an enzymatic hydrolysis unit under effective hydrolysis conditions to produce cellulosic sugars from the cellulose-rich solids and optionally from the hemicellulose oligomers; and (i) fermenting the cellulosic sugars to produce an additional quantity of ethanol.

Some variations provide a process for producing fermentable sugars from cellulosic biomass, the process comprising:

(a) providing a feedstock comprising cellulosic biomass;

(b) digesting the feedstock with a reaction solution including steam and/or hot water in a digestor under effective reaction conditions to produce a digested stream containing cellulose-rich solids, hemicellulose oligomers, and lignin;

(c) conveying the digested stream through a mechanical refiner, thereby generating a refined stream with reduced average particle size of the cellulose-rich solids;

(d) separating a vapor from the refined stream;

(e) introducing the refined stream to an acid hydrolysis unit under effective hydrolysis conditions to produce sugars from the cellulose-rich solids and optionally from the hemicellulose oligomers;

(f) recovering or further processing at least some of the sugars as fermentable sugars.

Certain embodiments provide a process for producing ethanol from cellulosic biomass, the process comprising:

(a) providing a feedstock comprising cellulosic biomass;

(b) digesting the feedstock with a reaction solution including steam and/or hot water in a digestor under effective reaction conditions to produce a digested stream containing cellulose-rich solids, hemicellulose oligomers, and lignin;

(c) conveying the digested stream through a blow-line refiner, thereby generating a refined stream with reduced average particle size of the cellulose-rich solids;

(d) separating a vapor from the refined stream;

(e) introducing the refined stream to an enzymatic hydrolysis unit under effective hydrolysis conditions to produce sugars from the cellulose-rich solids and from the hemicellulose oligomers;

(f) fermenting the sugars to produce ethanol in dilute solution; and (g) concentrating the dilute solution to produce an ethanol product.

In some variations, the invention provides a process for producing fermentable sugars from cellulosic biomass, the process comprising:

(a) providing a feedstock comprising cellulosic biomass;

(b) extracting the feedstock with an extraction solution including steam and/or hot water under effective extraction conditions to produce an extract liquor containing hemicellulose oligomers, dissolved lignin, and cellulose-rich solids;

(c) separating at least a portion of the cellulose-rich solids from the extract liquor, to produce washed cellulose-rich solids;

(d) removing a portion of glucan contained in the washed cellulose-rich solids by contacting the washed cellulose-rich solids with a liquefaction-focused blend of enzymes, to release glucose oligomers;

(e) co-hydrolyzing the glucose oligomers and the hemicellulose oligomers, such as with enzymes or an acid catalyst, to produce glucose and hemicellulose monomers; and (f) recovering the glucose and hemicellulose monomers as fermentable sugars.

In some embodiments, the extraction solution comprises steam in saturated, superheated, or supersaturated form. In some embodiments, the extraction solution comprises hot water. Additives may be present, such as acid or base catalysts, or other compounds present in recycled streams. The fraction of starting hemicellulose that is extracted into solution may be from about 60% to about 95%, such as about 75%, 80%, 85%, or 90%.

In some embodiments, step (c) includes washing the cellulose-rich solids using an aqueous wash solution, to produce a wash filtrate; and optionally combining at least some of the wash filtrate with the extract liquor. In some of these embodiments, step (c) further includes pressing the cellulose-rich solids to produce the washed cellulose-rich solids and a press filtrate; and optionally combining at least some of the press filtrate with the extract liquor.

Step (c) may include countercurrent washing, such as in two, three, four, or more washing stages. Step (d) may be integrated with step (c), and in certain embodiments, step (c) and step (d) are conducted in a single unit. That is, the separation/washing in step (c) may be combined with the application of the liquefaction-focused blend of enzymes in step (d), in various ways.

Step (d) is configured to cause at least some liquefaction as a result of enzymatic action on the washed cellulose-rich solids. "Liquefaction" means partial hydrolysis of cellulose to form glucose oligomers (i.e. glucan) that dissolve into solution, but not total hydrolysis of cellulose to glucose monomers (saccharification). Various fractions of cellulose may be hydrolyzed during liquefaction. In some embodiments, as a result of step (d), the fraction of cellulose hydrolyzed may be from about 5% to about 90%, such as about 10% to about 75% (e.g. about 15%, 20%, 25%, 30%, 35%, 40%, 45%, 50%, 55%, 60%, 65%, or 70%).

A "liquefaction-focused blend of enzymes" means a mixture of enzymes that includes at least one enzyme capable of hydrolyzing cellulose to form soluble oligomers. The application of the liquefaction-focused blend of enzymes may be conducted prior to a first washing stage, during (integrated with) a first washing stage, between a first and second washing stage, during (integrated with) a second washing stage, after a second washing stage, or during (integrated with) or after a later washing stage.

In some embodiments, the liquefaction-focused blend of enzymes in step (d) includes both endoglucanases and exoglucanases. Endoglucanases are cellulases that attack low-crystallinity regions in the cellulose fibers by endoaction, creating free chain-ends. Exoglucanases or cellobiohydrolases are cellulases that hydrolyze the 1,4-glycocidyl linkages in cellobiose.

Various cellulase enzymes may be utilized in the liquefaction-focused blend of enzymes, such as one or more enzymes recited in Verardi et al., "Hydrolysis of Lignocellulosic Biomass: Current Status of Processes and Technologies and Future Perspectives," *Bioethanol*, Prof. Marco Aurelio Pinheiro Lima (Ed.), ISBN: 978-953-51-0008-9, InTech (2012), which is hereby incorporated by reference.

Some embodiments employ thermotolerant enzymes obtained from thermophilic microorganisms. The thermophilic microorganisms can be grouped in thermophiles (growth up to 60° C.), extreme thermophiles (65-80° C.) and hyperthermophiles (85-110° C.). The unique stability of the enzymes produced by these microorganisms at elevated temperatures, extreme pH and high pressure (up to 1000 bar) makes them valuable for processes at harsh conditions. Also, thermophilic enzymes have an increased resistance to many denaturing conditions such as the use of detergents which can be an efficient means to obviate the irreversible adsorption of cellulases on the substrates. Furthermore, the utilization of high operation temperatures, which cause a decrease in viscosity and an increase in the diffusion coefficients of substrates, have a significant influence on the cellulose solubilization. It is worth noting that most thermophilic cellulases do not show inhibition at high level of reaction products (e.g. cellobiose and glucose). As consequence, higher reaction rates and higher process yields are expected. The high process temperature also reduces contamination. See Table 6, "Thermostable cellulases" in Verardi et al., cited previously, for exemplary thermotolerant enzymes that may be used in the liquefaction-focused blend of enzymes.

In some embodiments, an enzyme is selected such that at a high temperature, the enzyme is able to catalyze liquefaction (partial hydrolysis) but not saccharification (total hydrolysis). When the temperature is reduced, the same enzyme is able to catalyze saccharification to produce glucose.

The process may further comprise refining or milling the washed cellulose-rich solids prior to or during step (d).

When step (e) employs enzymes, these enzymes will typically contain cellulases and hemicellulases. The cellulases here may include β-glucosidases that convert cellooligosaccharides and disaccharide cellobiose into glucose. There are a number of enzymes that can attack hemicelluloses, such as glucoronide, acetylesterase, xylanase, β-xylosidase, galactomannase and glucomannase. Exemplary acid catalysts for step (e) include sulfuric acid, sulfur dioxide, hydrochloric acid, phosphoric acid, and nitric acid.

In some embodiments, non-acid and non-enzyme catalysts may be employed for co-hydrolyzing the glucose oligomers and the hemicellulose oligomers. For example, base catalysts, solid catalysts, ionic liquids, or other effective materials may be employed.

The process further comprises a step of fermenting the fermentable sugars to a fermentation product (such as ethanol), in some embodiments.

Other variations provide a process for producing fermentable sugars from cellulosic biomass, the process comprising:
  (a) providing a feedstock comprising cellulosic biomass;
  (b) extracting the feedstock with steam and/or hot water under effective extraction conditions to produce an extract liquor containing hemicellulose oligomers, dissolved lignin, and cellulose-rich solids;
  (c) separating at least a portion of the cellulose-rich solids from the extract liquor, to produce washed cellulose-rich solids;
  (d) removing a portion of glucan contained in the washed cellulose-rich solids by contacting the washed cellulose-rich solids with a liquefaction-focused blend of enzymes, to release glucose oligomers;
  (e) hydrolyzing the glucose oligomers with a first hydrolysis catalyst, to produce glucose;
  (f) hydrolyzing the hemicellulose oligomers with a second hydrolysis catalyst, to produce hemicellulose monomers; and
  (g) recovering the glucose and hemicellulose monomers, individually or in combination, as fermentable sugars.

In some embodiments, the first hydrolysis catalyst includes cellulases. In some embodiments, the second hydrolysis catalyst includes hemicellulases. In other embodiments, the first hydrolysis catalyst and the second hydrolysis catalyst are acid catalysts, base catalysts, ionic liquids, solid catalysts, or other effective materials. The first hydrolysis catalyst may be the same as, or different than, the second hydrolysis catalyst.

In some embodiments, the glucose is recovered in a separate stream from the hemicellulose monomers. In other embodiments, the glucose and the hemicellulose monomers are recovered in the same stream. The process may include fermentation of the glucose and/or the fermentable hemicellulose sugars to a fermentation product.

The biomass feedstock may be selected from hardwoods, softwoods, forest residues, agricultural residues (such as sugarcane bagasse), industrial wastes, consumer wastes, or combinations thereof. In any of these processes, the feedstock may include sucrose. In some embodiments with sucrose present in the feedstock, a majority of the sucrose is recovered as part of the fermentable sugars. In order to preserve sucrose (when present), it is preferred to utilize enzymes rather than acid catalysts for cellulose hydrolysis.

In some embodiments, the process starts as biomass is received or reduced to approximately ¼" thickness. In a first step of the process, the biomass chips are fed (e.g., from a chip bin) to a pressurized extraction vessel operating continuously or in batch mode. The chips may first be steamed or water-washed to remove dirt and entrained air. The chips are immersed with aqueous liquor or saturated vapor and heated to a temperature between about 100° C. to about 250°

C., for example 150° C., 160° C., 170° C., 180° C., 190° C., 200° C., or 210° C. Preferably, the chips are heated to about 180° C. to 210° C.

The pressure in the pressurized vessel may be adjusted to maintain the aqueous liquor as a liquid, a vapor, or a combination thereof. Exemplary pressures are about 1 atm to about 30 atm, such as about 3 atm, 5 atm, 10 atm, or 15 atm.

The solid-phase residence time for the digestor (pressurized extraction vessel) may vary from about 2 minutes to about 4 hours, such as about 5 minutes to about 1 hour. In certain embodiments, the digestor residence time is controlled to be about 5 to 15 minutes, such as 5, 6, 7, 8, 9, 10, 11, 12, 13, 14 or 15 minutes. The liquid-phase residence time for the digestor may vary from about 2 minutes to about 4 hours, such as about 5 minutes to about 1 hour. The vapor-phase residence time for the digestor may vary from about 1 minute to about 2 hours, for example, such as about 3 minutes to about 30 minutes. The solid-phase, liquid-phase, and vapor-phase residence times may all be about the same, or they may be independently controlled according to reactor-engineering principles (e.g., recycling and internal recirculation strategies).

The aqueous liquor may contain acidifying compounds, such as (but not limited to) sulfuric acid, sulfurous acid, sulfur dioxide, acetic acid, formic acid, or oxalic acid, or combinations thereof. The dilute acid concentration can range from 0.01% to 10% as necessary to improve solubility of particular minerals, such as potassium, sodium, or silica. Preferably, the acid concentration is selected from about 0.01% to 4%, such as 0.1%, 0.5%, 1%, 1.5%, 2%, 2.5%, 3%, or 3.5%.

A second step may include depressurization of the extracted chips into a blow tank or other tank or unit. The vapor can be used for heating the incoming woodchips or cooking liquor, directly or indirectly. The volatilized organic acids (e.g., acetic acid), which are generated or included in the cooking step, may be recycled back to the cooking.

A third step may include mechanically refining the extracted chips. This step (using, for example, a blow-line refiner) may be done before or after depressurization. Optionally, refined solids may be washed. The washing may be accomplished with water, recycled condensates, recycled permeate, or combination thereof. Washing typically removes most of the dissolved material, including hemicelluloses and minerals. The final consistency of the dewatered cellulose-rich solids may be increased to 30% or more, preferably to 50% or more, using a mechanical pressing device. The mechanical pressing device may be integrated with the mechanical refiner, to accomplish combined refining and washing.

A fourth step may include hydrolyzing the extracted chips with enzymes to convert some of the cellulose to glucose. When enzymes are employed for the cellulose hydrolysis, the enzymes preferably include cellulase enzymes. Enzymes may be introduced to the extracted chips along with water, recycled condensates, recycled permeate, additives to adjust pH, additives to enhance hydrolysis (such as lignosulfonates), or combinations thereof.

Some or all of the enzymes may be added to the blow line before or at the blow-line refiner, for example, to assist in enzyme contact with fibers. In some embodiments, at least a portion of enzymes are recycled in a batch or continuous process.

When an acid is employed for the cellulose hydrolysis, the acid may be selected from sulfuric acid, sulfurous acid, sulfur dioxide, formic acid, acetic acid, oxalic acid, or combinations thereof. Acids may be added to the extracted chips before or after mechanical refining. In some embodiments, dilute acidic conditions are used at temperatures between about 100° C. and 190° C., for example about 120° C., 130° C., 140° C., 150° C., 160° C., or 170° C., and preferably from 120° C. to 150° C. In some embodiments, at least a portion of the acid is recycled in a batch or continuous process.

The acid may be selected from sulfuric acid, sulfurous acid, or sulfur dioxide. Alternatively, or additionally, the acid may include formic acid, acetic acid, or oxalic acid from the cooking liquor or recycled from previous hydrolysis.

A fifth step may include conditioning of hydrolysate to remove some or most of the volatile acids and other fermentation inhibitors. The evaporation may include flashing or stripping to remove sulfur dioxide, if present, prior to removal of volatile acids. The evaporation step is preferably performed below the acetic acid dissociation pH of 4.8, and most preferably a pH selected from about 1 to about 2.5. In some embodiments, additional evaporation steps may be employed. These additional evaporation steps may be conducted at different conditions (e.g., temperature, pressure, and pH) relative to the first evaporation step.

In some embodiments, some or all of the organic acids evaporated may be recycled, as vapor or condensate, to the first step (cooking step) to assist in the removal of hemicelluloses or minerals from the biomass. This recycle of organic acids, such as acetic acid, may be optimized along with process conditions that may vary depending on the amount recycled, to improve the cooking effectiveness.

A sixth step may include recovering fermentable sugars, which may be stored, transported, or processed. A sixth step may include fermenting the fermentable sugars to a product, as further discussed below.

A seventh step may include preparing the solid residuals (containing lignin) for combustion. This step may include refining, milling, fluidizing, compacting, and/or pelletizing the dried, extracted biomass. The solid residuals may be fed to a boiler in the form of fine powder, loose fiber, pellets, briquettes, extrudates, or any other suitable form. Using known equipment, solid residuals may be extruded through a pressurized chamber to form uniformly sized pellets or briquettes.

Some embodiments of the invention enable processing of "agricultural residues," which for present purposes is meant to include lignocellulosic biomass associated with food crops, annual grasses, energy crops, or other annually renewable feedstocks. Exemplary agricultural residues include, but are not limited to, corn stover, corn fiber, wheat straw, sugarcane bagasse, rice straw, oat straw, barley straw, miscanthus, energy cane, or combinations thereof. In certain embodiments, the agricultural residue is sugarcane bagasse, energy cane bagasse, sugarcane straw, or energy cane straw. Agricultural materials with both residue material as well as sugars can be used, such as whole energy cane, whole sugarcane, whole corn, or portions thereof.

In some embodiments, the fermentable sugars are recovered from solution, in purified form. In some embodiments, the fermentable sugars are fermented to produce of biochemicals or biofuels such as (but by no means limited to) ethanol, 1-butanol, isobutanol, acetic acid, lactic acid, or any other fermentation products. A purified fermentation product may be produced by distilling the fermentation product, which will also generate a distillation bottoms stream containing residual solids. A bottoms evaporation stage may be used, to produce residual solids.

Following fermentation, residual solids (such as distillation bottoms) may be recovered, or burned in solid or slurry form, or recycled to be combined into the biomass pellets. Use of the fermentation residual solids may require further removal of minerals. Generally, any leftover solids may be used for burning, after concentration of the distillation bottoms.

Alternatively, or additionally, the process may include recovering the residual solids as a fermentation co-product in solid, liquid, or slurry form. The fermentation co-product may be used as a fertilizer or fertilizer component, since it will typically be rich in potassium, nitrogen, and/or phosphorous.

In certain embodiments, the process further comprises combining, at a pH of about 4.8 to 10 or higher, a portion of vaporized acetic acid with an alkali oxide, alkali hydroxide, alkali carbonate, and/or alkali bicarbonate, wherein the alkali is selected from the group consisting of potassium, sodium, magnesium, calcium, and combinations thereof, to convert the portion of the vaporized acetic acid to an alkaline acetate. The alkaline acetate may be recovered. If desired, purified acetic acid may be generated from the alkaline acetate.

In some variations, the invention provides a process for separating fermentation inhibitors from a biomass-derived hydrolysate, the process comprising:
 (a) providing a biomass-derived liquid hydrolysate stream comprising a fermentation inhibitor;
 (b) introducing the liquid hydrolysate stream to a stripping column;
 (c) introducing a steam-rich vapor stream to the stripping column to strip at least a portion of the fermentation inhibitor from the liquid hydrolysate stream;
 (d) recovering, from the stripping column, a stripped liquid stream and a stripper vapor output stream, wherein the stripped liquid stream has lower fermentation inhibitor concentration than the liquid hydrolysate stream;
 (e) compressing the stripper vapor output stream to generate a compressed vapor stream;
 (f) introducing the compressed vapor stream, and a water-rich liquid stream, to an evaporator;
 (g) recovering, from the evaporator, an evaporated liquid stream and an evaporator output vapor stream; and
 (h) recycling at least a portion of the evaporator output vapor stream to the stripping column as the steam-rich vapor stream, or a portion thereof.

The biomass-derived hydrolysate may be the product of acidic or enzymatic hydrolysis, or it may be the extracted solution from the digestor, for example. In some embodiments, the fermentation inhibitor is selected from the group consisting of acetic acid, formic acid, formaldehyde, acetaldehyde, lactic acid, furfural, 5-hydroxymethylfurfural, furans, uronic acids, phenolic compounds, sulfur-containing compounds, and combinations or derivatives thereof.

In certain embodiments, the fermentation inhibitor is acetic acid. The stripped liquid stream preferably has less than 10 g/L acetic acid concentration, such as less than 5 g/L acetic acid concentration.

In some embodiments, the water-rich liquid stream contains biomass solids that are concentrated in the evaporator. These biomass solids may be derived from the same biomass feedstock as is the biomass-derived liquid hydrolysate, in an integrated process.

Optionally, the fermentation inhibitor is recycled to a previous unit operation (e.g., digestor or reactor) for generating the biomass-derived liquid hydrolysate stream, to assist with hydrolysis or pretreatment of a biomass feedstock or component thereof. For example, acetic acid may be recycled for this purpose, to aid in removal of hemicelluloses from biomass and/or in oligomer hydrolysis to monomer sugars.

Some variations provide a process for separating fermentation inhibitors from a biomass-derived hydrolysate, the process comprising:
 (a) providing a biomass-derived liquid hydrolysate stream comprising a fermentation inhibitor;
 (b) introducing the liquid hydrolysate stream to a stripping column;
 (c) introducing a steam-rich vapor stream to the stripping column to strip at least a portion of the fermentation inhibitor from the liquid hydrolysate stream;
 (d) recovering, from the stripping column, a stripped liquid stream and a stripper vapor output stream, wherein the stripped liquid stream has lower fermentation inhibitor concentration than the liquid hydrolysate stream;
 (e) introducing the stripper vapor output stream, and a water-rich liquid stream, to an evaporator;
 (f) recovering, from the evaporator, an evaporated liquid stream and an evaporator output vapor stream;
 (g) compressing the evaporator output vapor stream to generate a compressed vapor stream; and
 (h) recycling at least a portion of the compressed vapor stream to the stripping column as the steam-rich vapor stream, or a portion thereof.

In some embodiments, the evaporator is a boiler, the water-rich liquid stream comprises boiler feed water, and the evaporated liquid stream comprises boiler condensate.

The process may be continuous, semi-continuous, or batch. When continuous or semi-continuous, the stripping column may be operated countercurrently, cocurrently, or a combination thereof.

In certain variations of the present invention, a process for separating and recovering a fermentation inhibitor from a biomass-derived hydrolysate comprises:
 (a) providing a biomass-derived liquid hydrolysate stream comprising a fermentation inhibitor;
 (b) introducing the liquid hydrolysate stream to a stripping column;
 (c) introducing a steam-rich vapor stream to the stripping column to strip at least a portion of the fermentation inhibitor from the liquid hydrolysate stream;
 (d) recovering, from the stripping column, a stripped liquid stream and a stripper vapor output stream, wherein the stripped liquid stream has lower fermentation inhibitor concentration than the liquid hydrolysate stream;
 (e) introducing the stripper vapor output stream, and a water-rich liquid stream, to a rectification column;
 (f) recovering, from the rectification column, a rectified liquid stream and a rectification column vapor stream, wherein the rectified liquid stream has higher fermentation inhibitor concentration than the liquid hydrolysate stream; and
 (g) recycling at least a portion of the rectification column vapor stream to the stripping column as the steam-rich vapor stream, or a portion thereof.

The fermentation inhibitor may be selected from the group consisting of acetic acid, formic acid, formaldehyde, acetaldehyde, lactic acid, furfural, 5-hydroxymethylfurfural, furans, uronic acids, phenolic compounds, sulfur-containing compounds, and combinations or derivatives thereof. In some embodiments, the fermentation inhibitor comprises or consists essentially of acetic acid.

In the case of acetic acid, the stripped liquid stream preferably has less than 10 g/L acetic acid concentration, such as less than 5 g/L acetic acid concentration. The rectification column vapor stream preferably has less than 0.5 g/L acetic acid concentration, such as less than 0.1 g/L acetic acid concentration. The rectified liquid stream preferably has at least 25 g/L acetic acid concentration, such as about 40 g/L or more acetic acid. In some embodiments, the rectified liquid stream has at least 10 times higher concentration of acetic acid compared to the stripped liquid stream. In certain embodiments, the process further comprises recovering the acetic acid contained in the rectified liquid stream using liquid-vapor extraction or liquid-liquid extraction.

In some embodiments, the water-rich liquid stream includes evaporator condensate. The evaporator condensate may be derived from an evaporator in which biomass solids are concentrated, and the biomass solids may be derived from the same biomass feedstock as the biomass-derived liquid hydrolysate, in an integrated process.

Optionally, the fermentation inhibitor (e.g., acetic acid) is recycled to a previous unit operation for generating the biomass-derived liquid hydrolysate stream, to assist with hydrolysis or pretreatment of a biomass feedstock or component thereof.

The process may be continuous, semi-continuous, or batch. When continuous or semi-continuous, the stripping column may be operated countercurrently, cocurrently, or a combination thereof. The rectification column may be operated continuous, semi-continuous, or batch.

In various embodiments, step (g) comprises compressing and/or conveying the rectification column vapor stream using a device selected from the group consisting of a mechanical centrifugal vapor compressor, a mechanical axial vapor compressor, a thermocompressor, an ejector, a diffusion pump, a turbomolecular pump, and combinations thereof.

If desired, a base or other additive may be included in the water-rich liquid stream, or separately introduced to the rectification column, to produce salts or other reaction products derived from fermentation inhibitors. In some embodiments, the water-rich liquid stream includes one or more additives capable of reacting with the fermentation inhibitor. In certain embodiments, the fermentation inhibitor includes acetic acid, and the one or more additives include a base. An acetate salt may then be generated within the rectification column, or in a unit coupled to the rectification column. Optionally, the acetate salt may be separated and recovered using liquid-vapor extraction or liquid-liquid extraction.

This patent application hereby incorporates by reference herein the following patents: "PROCESS FOR OBTAINING BIOCHEMICALS IN A ZERO LIQUID DISCHARGE PLANT," U.S. Pat. No. 8,211,680; "PROCESS FOR PRODUCING HEMICELLULOSE SUGARS AND ENERGY FROM BIOMASS," U.S. Pat. No. 8,518,672; "PROCESS FOR PRODUCING ALCOHOL AND OTHER BIOPRODUCTS FROM BIOMASS EXTRACTS IN A KRAFT PULP MILL," U.S. Pat. No. 8,518,213; "DEICER COMPOSITIONS AND PROCESSES FOR MAKING DEICERS," U.S. Pat. No. 8,679,364; "CORROSION-INHIBITING DEICERS DERIVED FROM BIOMASS," U.S. Pat. No. 8,845,923; "PROCESSES FOR PRODUCING FERMENTABLE SUGARS AND LOW-ASH BIOMASS FOR COMBUSTION OR PELLETS," U.S. Pat. No. 8,685,685; "PROCESS FOR OBTAINING BIOCHEMICALS IN A ZERO LIQUID DISCHARGE PLANT," U.S. Pat. No. 8,785,155; and "PROCESSES FOR PRODUCING FERMENTABLE SUGARS AND ENERGY-DENSE BIOMASS FOR COMBUSTION," U.S. Pat. No. 8,906,657.

This patent application hereby incorporates by reference herein the following patent applications: "STEPWISE ENZYMATIC HYDROLYSIS PROCESS FOR CONVERTING CELLULOSE TO GLUCOSE," U.S. patent application Ser. No. 13/626,220 (now allowed); "PROCESSES FOR PRODUCING CELLULOSE PULP, SUGARS, AND CO-PRODUCTS FROM LIGNOCELLULOSIC BIOMASS," U.S. patent application Ser. No. 14/044,784 and U.S. patent application Ser. No. 14/044,790; "PRODUCTION OF FERMENTABLE $C_5$ AND $C_6$ SUGARS FROM LIGNOCELLULOSIC BIOMASS," U.S. patent application Ser. No. 14/583,572; and "PROCESSES AND APPARATUS FOR REMOVAL OF FERMENTATION INHIBITORS FROM BIOMASS HYDROLYSATES," U.S. patent application Ser. No. 14/623,853.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A process for producing a fermentation product from biomass, said process comprising:
   (a) providing a feedstock containing lignocellulosic biomass and monomeric sugar that is physically bound therein;
   (b) combining said feedstock with a sugar-fermenting microorganism and optionally cellulase enzymes, to create an initial mixture;
   (c) refining said initial mixture to mechanically release said monomeric sugar and to intimately mix said sugar-fermenting microorganism and, if present, said cellulase enzymes, wherein refining employs a first refiner selected from the group consisting of a hot-blow refiner, a hot-stock refiner, a blow-line refiner, a disk refiner, a conical refiner, a cylindrical refiner, an in-line defibrator, a homogenizer, and combinations thereof;
   (d) fermenting said monomeric sugar with said sugar-fermenting microorganism to produce an initial quantity of a fermentation product contained within an intermediate mixture;

(e) digesting said intermediate mixture with a reaction solution consisting of steam and/or hot water in a digestor under effective reaction conditions to produce a digested stream containing cellulose-rich solids, hemicellulose oligomers, and lignin;

(f) optionally conveying said digested stream through a second refiner to reduce average particle size of said cellulose-rich solids;

(g) separating a vapor from said digested stream and recovering said fermentation product from said vapor;

(h) introducing said digested stream to an enzymatic hydrolysis unit under effective hydrolysis conditions to produce cellulosic sugars from said cellulose-rich solids and optionally from said hemicellulose oligomers; and (i) fermenting said cellulosic sugars to produce an additional quantity of said fermentation product;

wherein steps (a)-(i) are conducted in order.

2. The process of claim 1, wherein said feedstock includes sugarcane, energy cane, or combinations thereof, and wherein said monomeric sugar is sucrose.

3. The process of claim 1, wherein said feedstock includes corn, and wherein said monomeric sugar is dextrose.

4. The process of claim 1, wherein said sugar-fermenting microorganism is a yeast.

5. The process of claim 1, wherein said sugar-fermenting microorganism is a bacteria.

6. The process of claim 1, wherein said reaction solution consists of steam in saturated, superheated, or supersaturated form.

7. The process of claim 1, wherein said reaction solution consists of hot water.

8. The process of claim 1, wherein said second refiner is selected from the group consisting of a hot-blow refiner, a hot-stock refiner, a blow-line refiner, a disk refiner, a conical refiner, a cylindrical refiner, an in-line defibrator, a homogenizer, and combinations thereof.

9. The process of claim 8, wherein said second refiner is a blow-line refiner.

10. The process of claim 1, wherein step (f) is conducted, and wherein a blow tank is situated downstream of said mechanical refiner.

11. The process of claim 1, wherein said vapor is separated from a blow tank, and wherein heat is recovered from at least some of said vapor.

12. The process of claim 1, wherein enzymes introduced or present in said enzymatic hydrolysis unit include cellulases and hemicellulases.

13. The process of claim 1, wherein enzymes introduced or present in said enzymatic hydrolysis unit include endoglucanases and exoglucanases.

14. The process of claim 1, wherein said fermentation product is selected from ethanol, n-butanol, 1,4-butanediol, succinic acid, lactic acid, or combinations thereof.

15. The process of claim 1, wherein said fermentation product is ethanol.

16. A process for producing a fermentation product from biomass, said process comprising:

(a) providing a feedstock containing lignocellulosic biomass and monomeric sugar that is physically bound therein;

(b) combining said feedstock with a sugar-fermenting microorganism and cellulase enzymes, to create an initial mixture;

(c) refining said initial mixture to mechanically release said monomeric sugar and to intimately mix said sugar-fermenting microorganism and said cellulase enzymes, wherein refining employs a first refiner selected from the group consisting of a hot-blow refiner, a hot-stock refiner, a blow-line refiner, a disk refiner, a conical refiner, a cylindrical refiner, an in-line defibrator, a homogenizer, and combinations thereof;

(d) fermenting said monomeric sugar with said sugar-fermenting microorganism to produce an initial quantity of a fermentation product contained within an intermediate mixture;

(e) digesting said intermediate mixture with a reaction solution consisting of steam and/or hot water in a digestor under effective reaction conditions to produce a digested stream containing cellulose-rich solids, hemicellulose oligomers, and lignin;

(f) conveying said digested stream through a second refiner to reduce average particle size of said cellulose-rich solids;

(g) introducing said digested stream to an enzymatic hydrolysis unit under effective hydrolysis conditions to produce cellulosic sugars from said cellulose-rich solids and optionally from said hemicellulose oligomers; and (h) fermenting said cellulosic sugars to produce an additional quantity of said fermentation product;

wherein steps (a)-(h) are conducted in order.

17. A process for producing a fermentation product from biomass, said process comprising:

(a) providing a feedstock containing lignocellulosic biomass and monomeric sugar that is physically bound therein;

(b) combining said feedstock with a sugar-fermenting microorganism, to create an initial mixture;

(c) refining said initial mixture to mechanically release said monomeric sugar and to intimately mix said sugar-fermenting microorganism, wherein refining employs a refiner selected from the group consisting of a hot-blow refiner, a hot-stock refiner, a blow-line refiner, a disk refiner, a conical refiner, a cylindrical refiner, an in-line defibrator, a homogenizer, and combinations thereof;

(d) fermenting said monomeric sugar with said sugar-fermenting microorganism to produce an initial quantity of a fermentation product contained within an intermediate mixture;

(e) digesting said intermediate mixture with a reaction solution consisting of steam and/or hot water in a digestor under effective reaction conditions to produce a digested stream containing cellulose-rich solids, hemicellulose oligomers, and lignin;

(f) introducing said digested stream to an enzymatic hydrolysis unit under effective hydrolysis conditions to produce cellulosic sugars from said cellulose-rich solids and optionally from said hemicellulose oligomers; and (g) fermenting said cellulosic sugars to produce an additional quantity of said fermentation product;

wherein steps (a)-(g) are conducted in order.

* * * * *